(12) United States Patent
Cohen

(10) Patent No.: US 6,993,851 B2
(45) Date of Patent: Feb. 7, 2006

(54) METHOD AND DEVICE FOR MEASURING FLUCTUATIONS IN THE CROSS-SECTIONAL AREA OF HAIR IN A PRE-DETERMINED SCALP AREA

(75) Inventor: Bernard H. Cohen, Miami, FL (US)

(73) Assignee: Bernard Cohen Technology, LLC, Miami, FL (US)

( * ) Notice: Subject to any disclaimer, the term of this patent is extended or adjusted under 35 U.S.C. 154(b) by 0 days.

(21) Appl. No.: 10/826,943

(22) Filed: Apr. 16, 2004

(65) Prior Publication Data

US 2006/0005409 A1    Jan. 12, 2006

(51) Int. Cl.
*A61B 1/00*    (2006.01)

(52) U.S. Cl. ........................................ 33/512; 33/784

(58) Field of Classification Search .................. 33/512, 33/511, 783–784, 813, 818, 819, 828, 831

See application file for complete search history.

(56) References Cited

U.S. PATENT DOCUMENTS

| 1,962,357 | A | * | 6/1934 | Nessler | 33/512 |
| 1,962,518 | A | * | 6/1934 | Nessler | 33/512 |
| 1,981,911 | A | * | 11/1934 | Engelsman | 33/512 |
| 4,665,741 | A | * | 5/1987 | Kabacoff et al. | 73/149 |
| 5,327,656 | A | * | 7/1994 | Nissimov | 33/512 |
| 5,495,677 | A | * | 3/1996 | Tachikake et al. | 33/784 |

* cited by examiner

*Primary Examiner*—Diego Gutierrez
*Assistant Examiner*—Tania Courson
(74) *Attorney, Agent, or Firm*—Welsh & Katz, Ltd.

(57) ABSTRACT

The method for isolating an area of hair-bearing skin and measuring a combined cross section of hair in the area comprising the steps of: preparing a pre-measured site on the scalp; isolating a standardized bundle of uncut hair at the site; compressing the bundle of hair with a measurable load while simultaneously measuring the height of the bundle of hair with a piston and cylinder device.

One embodiment of the device comprises a body having a slot for receiving a bundle of hair, an anvil positioned adjacent said slot, and a mechanism for causing relative movement between the body having the slot and the anvil thereby to compress a bundle of uncut hair received in the slot against the anvil.

24 Claims, 9 Drawing Sheets

METHOD AND DEVICE FOR MEASURING FLUCTUATIONS IN THE CROSS-SECTIONAL AREA OF HAIR IN A PRE-DETERMINED SCALP AREA

BACKGROUND OF THE INVENTION

1. Field of the Invention

The present invention relates to a method and device for measuring fluctuations in the cross sectional area of a bundle of hair for the purpose of documenting the clinical course of medical hair loss disorders and the effectiveness of hair growth treatments and/or for the purpose of indirectly calculating the severity of balding disorders or efficacy of hair growth treatment as evidenced by a decrease or increase in hair population and/or hair shaft diameter.

2. Description of the Related Art

Heretofore, a hair volume-measuring device used for measure of hair damage was disclosed in the Kabacoff et al. U.S. Pat. No. 4,665,741.

Hair shedding is a condition characterized by loss of hairs of normal-sized diameters. It is one of the two major categories of hair loss. Shedding is diffusely distributed over the scalp and may be the sign of several medical abnormalities and toxicities. It may physiologically follow high fever, cessation of birth control pills, or childbirth. Shedding is characterized by the appearance of skin on the scalp where hair was once present. Shedding may be quantified by measuring the density of hairs present in an area of one-centimeter square of scalp. Hair density usually is measured by closely cutting the scalp hair (about 2 mm long in an area 5 mm×5 mm) and then counting the remaining cut hairs present on the scalp and multiplying that value times 4. The hair density of normal individuals in the absence of shedding ranges between 120 to 200 hairs per sq cm of scalp.

Hair thinning is a condition characterized by the gradual miniaturization of individual scalp hairs. It is the second major category of hair loss. The appearance of hair loss is the result of decreasing diameters resulting in the eventual absence of hairs. Thinning (like shedding) also is characterized by the appearance of skin on the scalp where hair was once present. Thinning affects an estimated 75% of men and 10% of women. Unlike shedding, it is not diffuse in its distribution over the entire scalp surface, but almost always appears in a pattern, with hair loss on the top of the scalp. Thinning characteristically spares the posterior and sides of the lower scalp, creating a familiar horse-shaped fringe that persists in spite of the most advanced cases.

Thinning occurs in healthy individuals and is referred to as balding, pattern balding, male or female pattern alopecia, androgenctic alopecia, male or female pattern balding. It is considered normal in 75% of men. And, although it may occur in healthy women, it may indicate an endocrine abnormality in a small group of women.

Early pattern balding is difficult to recognize and difficult to quantify. Simple density measurements (as performed in shedding) are of little value because there is a mixed population of both normal-sized and miniaturized hairs. When density counts are performed, a normal and miniaturized hair would each be counted as one hair. Therefore, in order to detect and quantify thinning in a meaningful manner, the actual hair mass (the collective cross sections of hair from a pre-determined area of scalp) must be measured. This alone would reflect the density of hairs and the array of mixed diameters that are present.

In order to quantify pattern and diffuse hair loss, scientists have commonly used three basic methods:

1. Hair density count
2. Clinical photography
3. Hair weight.

Quantification of hair loss by measuring the collective cross sections in a pre-determined area of scalp has not been reported in the scientific literature nor disclosed in prior U.S. patents.

The three commonly used methods are described in more detail below:

Density count: The density of an area of scalp is compared to the known normal range of values, which is 120 to 200 hairs per sq cm. To determine the percent loss of density for a single individual, the density on the top part of the scalp (the area of loss) may be compared to the density on the lower back and sides (the normal and permanent hair zone). The percent hair loss is calculated by dividing the hair count in the hair loss area by the hair count in the permanent zone. This method is quite imprecise in conditions of thinning, because it measures only the number of hairs and makes no allowance for their variations in diameter. The method is used however because it is a bit more precise than clinical photography. It requires cutting off hair and direct scalp exam with a hand lens or video microscope.

Clinical photography: Photography is performed comparing the patient's hair loss area to the permanent zone. It may also compare the patient's hair loss zone to a picture of the same zone of a patient with no hair loss, or of a prior or subsequent state of loss in the same patient. In this manner, the growth or loss is grossly quantified by visual observation alone. No insight is gained into whether or not the hair loss is the result of thinning or shedding. Photography is quite imprecise and obscured by various hairstyles and hair lengths. It is however the most common form of hair loss documentation because it is rapid, requires not special training and is easily archived. It does not require the cutting of hair, but does require standard photo equipment lighting, positioning of hair, and standardized hair length, to yield any kind of comparable data.

Hair weight: A small area of hair (usually 5 mm×5 mm) is shaved from a balding area. The patient returns in 30 days and the newly grown hair is cut and weighed. The value is compared to a subsequent similar assay of the same area. In cases of pattern loss, the procedure may be performed in the permanent zone (lower posterior and lateral horseshoe shaped zone) and compared to the value in the thinning zone. The percent hair loss may be calculated by dividing the hair weight in the thinning area by the hair weight in the permanent zone. Hair weight is a very precise method of measuring hair loss because it considers both the number of hairs and their diameters and the hair length in its calculation. Its disadvantage is that the sample size represents a relatively small sample of the scalp surface, and because it measures hair length as well, it may not be as meaningful as thought.

Furthermore it is a very tedious process and impractical to perform in a clinical setting. It also requires cutting off hair. It is used primarily by commercial laboratories to measure the effectiveness of hair-growing preparations i.e. finasteride, dutasteride, and minoxidil.

BRIEF SUMMARY OF THE INVENTION

According to the present invention there is provided a method and device for measuring fluctuations in the cross sectional area of a section of hair as it relates to the quantification and clinical course of medical hair loss disorders or the effectiveness or progress of hair loss treatment.

The method and device are used for determining the cumulative cross-section of hairs within a pre-measured area. The method and device uses a much larger sample of scalp surface than the hair weight method, hair count method, and hair cutting is not required. The length of the hair is not considered a factor in the evaluation because of wide variations of individual styling would make it impossible, and clinically irrelevant. The method of the present invention is easy to perform in a non-laboratory setting and employs a new hand-held device. The method and device allow physicians and hair care professionals to track and document the status of patients, suffering from scalp hair thinning or shedding, at any time in the course of their evaluation or treatment. The method and device may be used to quantitatively evaluate the effectiveness of hair growing preparations and drugs and quantify the severity and clinical course of other medical hair loss disorders.

In practicing the method of the present invention, a predetermined area of hair-bearing skin or scalp is isolated by any of several means. Typically a 2×2 cm of scalp hair is manually isolated using a comb or combing element and fixed in place using 1×3" gummed papers printed with a centimeter scale which are aligned and overlapped in the configuration of a 2×2 cm square. Alternatively, a 2×2 cm area may be isolated by using any device that demarcates the periphery of the area, such as with a ruler and washable ink, marking pen, and/or using a simple comb-like device that is 2 cm. in length, which simultaneously bundles the hair and demarcates the perimeter of the area.

The bundle is snared by a lightweight spring-loaded hook-like ("J" shaped) arm which is drawn into a body of the device of the present invention. The device comprises a hair-trapping element including a "J" shaped end that extends through a boss and has a hair-receiving slot. The device further includes an anvil on an end surface of the boss positioned adjacent the slot whereby relative movement between the "J" shaped end and the anvil compresses the hair received in the slot. A heavyweight compression spring is provided in the device which bears against the boss. Alternatively the device can have an anvil that moves into a stationary slot.

The bundle is captured in the slot and automatically immobilized against the anvil on the boss. Preferably, the slot is 1 mm wide and 12 mm high and relative movement between the anvil and the slot measures the height of the hair. By engaging the heavy compression spring, the load on the column of trapped hair may be precisely maintained and thereby kept constant in repeated measurements. This is important because the hair bundle is quite compressible. The mm height of the hair column is displayed on an LED window of an integrated micrometer head that causes relative movement between the anvil and the slot. If a mechanical height measuring gauge is incorporated in the design of the device, it is displayed on the face of an analog dial. If an electronic height measuring gauge is incorporated into the device, the height is displayed on an LED window. The height of hair in the trapping hair-receiving slot is expressed as an arbitrary value that shall be called the hair mass, the hair mass index, the cross-sectional index, the cumulative cross-sectional index, or the combined cross-sectional index.

The method is performed in the hair thinning area and the permanent hair growth area of the scalp. The index value of the thinning area is divided by the index value of the permanent area. The percent loss of hair mass in the thinning area is thus derived. It is believed that the method and device of the present invention may have profound medical significance for the following reason: It is a known medical fact that an individual must lose half of the hair in an area of the scalp, before it is obvious to the casual observer that any hair has been lost. This can also be demonstrated by the casual observers inability to tell the difference between a toupee with 200 hairs per sq cm and a toupee with 100 hairs per sq cm. This observation however translates to the following: By the time an individual realizes that he is "losing hair" he has already lost half of his hair! The device of the present invention enables hair professionals and physicians to measure the hair mass in the pre-balding normal-looking areas of the scalp and compare these values to the hair mass value in the permanent zone. In this way one can detect whether or not there is hair loss years before it is visually obvious to the patient or his physician. The patient is alerted to the early hair loss and may enjoy the advantages of starting therapy before the loss has significantly advanced. The method and device may also be used to track and quantify the progressive hair loss of individuals with untreated balding, or track and quantify the therapeutic response of hair to drugs and devices that allegedly grow hair.

DETAILED DESCRIPTION OF THE INVENTION

Figure 1:
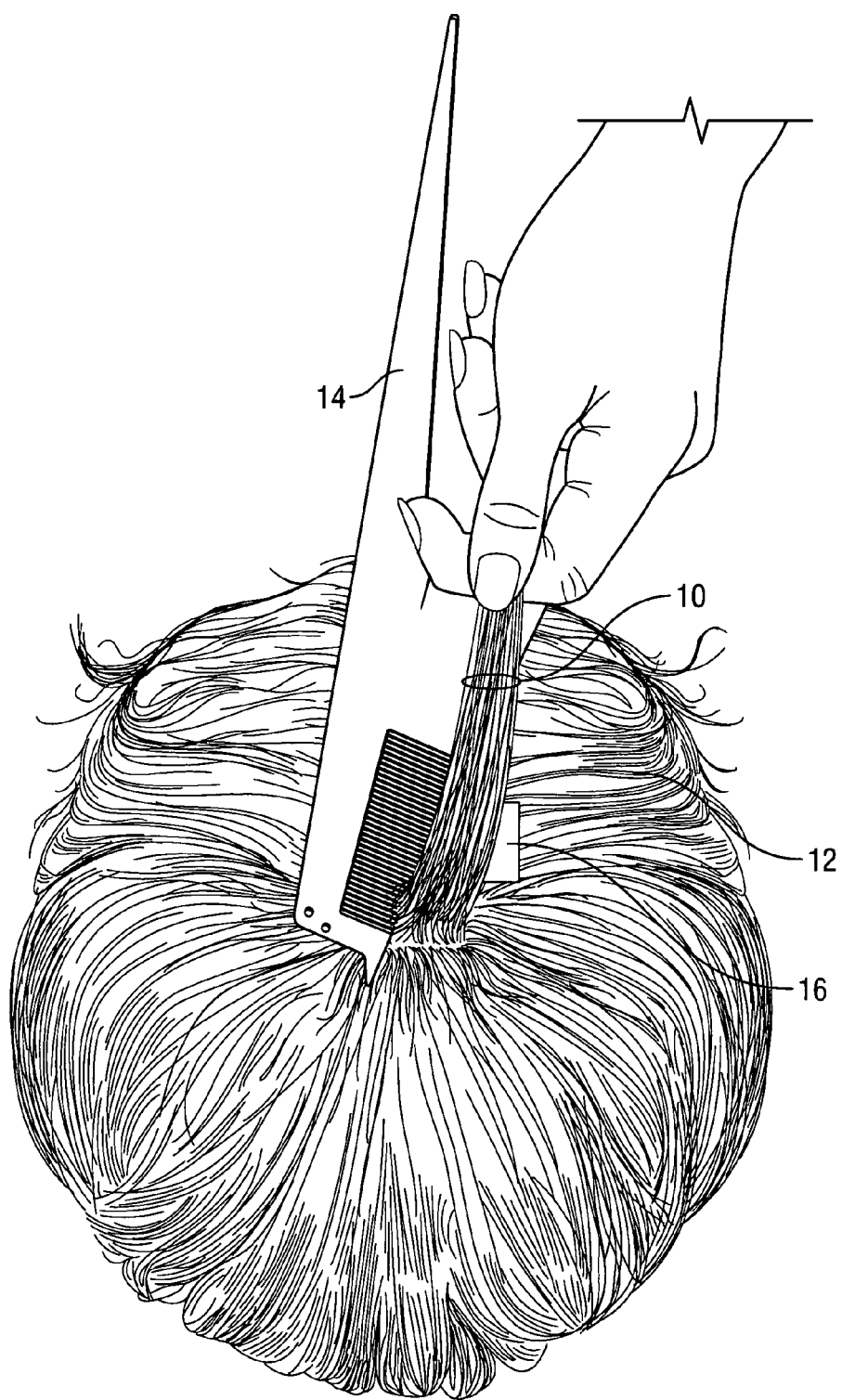
FIG. 1 is a top view of a scalp showing a section or bundle of hair that is combed from a delineated section of scalp with a combing element and shows one side of the section of scalp being delineated by a gummed label.

Referring now to FIG. 1 there is illustrated therein a combed bundle or section of hair 10 from a scalp 12, that has been combed with a comb or combing element 14. The bundle 10 of hair is delineated from a predetermined area of the scalp 12 by a gummed label 16, without cutting the bundle 10 of hair.

Figure 2:
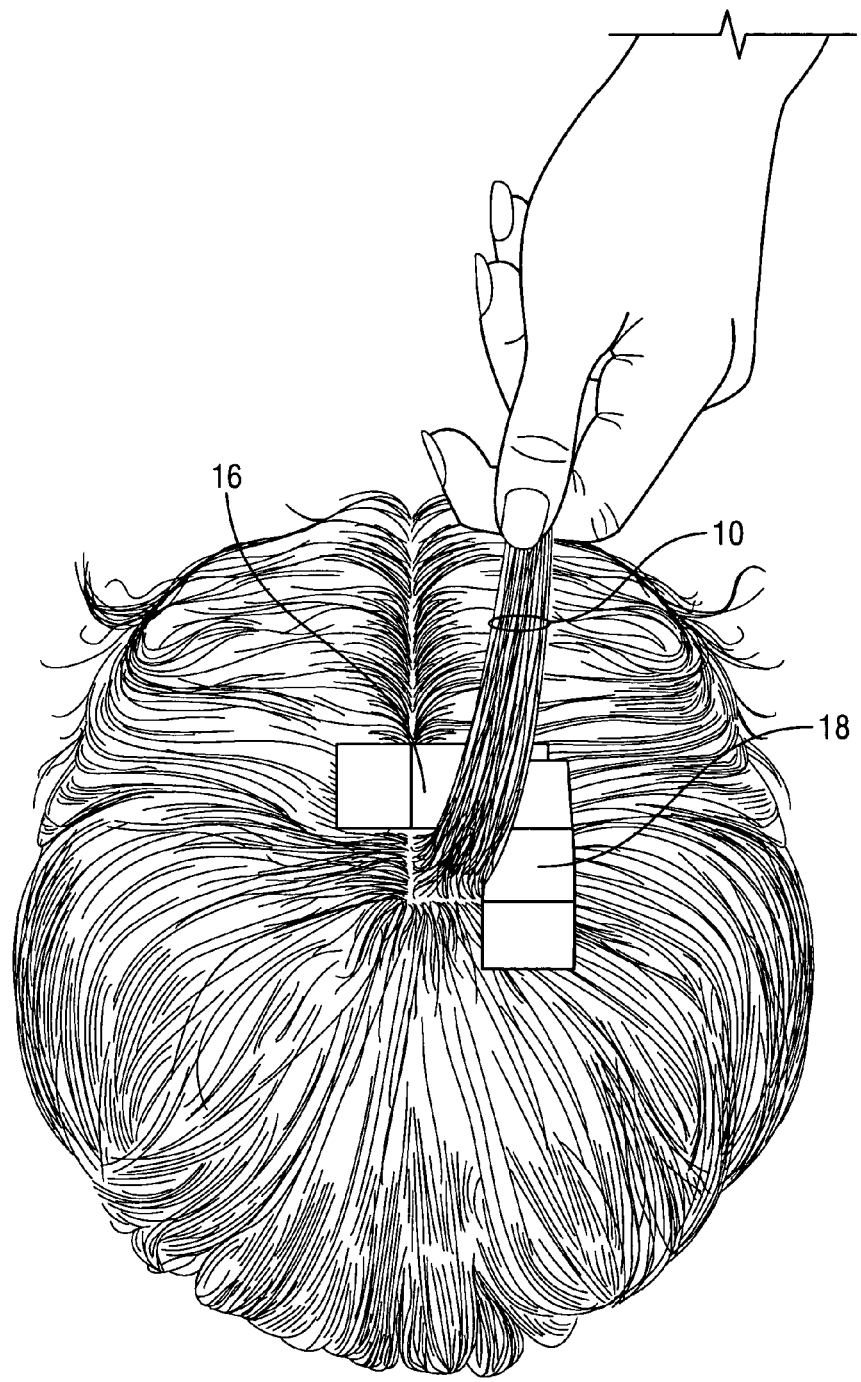
FIG. 2 is a top view of a scalp showing a section or bundle of hair that is combed from a delineated section of scalp and shows two sides of the section of scalp being delineated by gummed labels.
Figure 3:
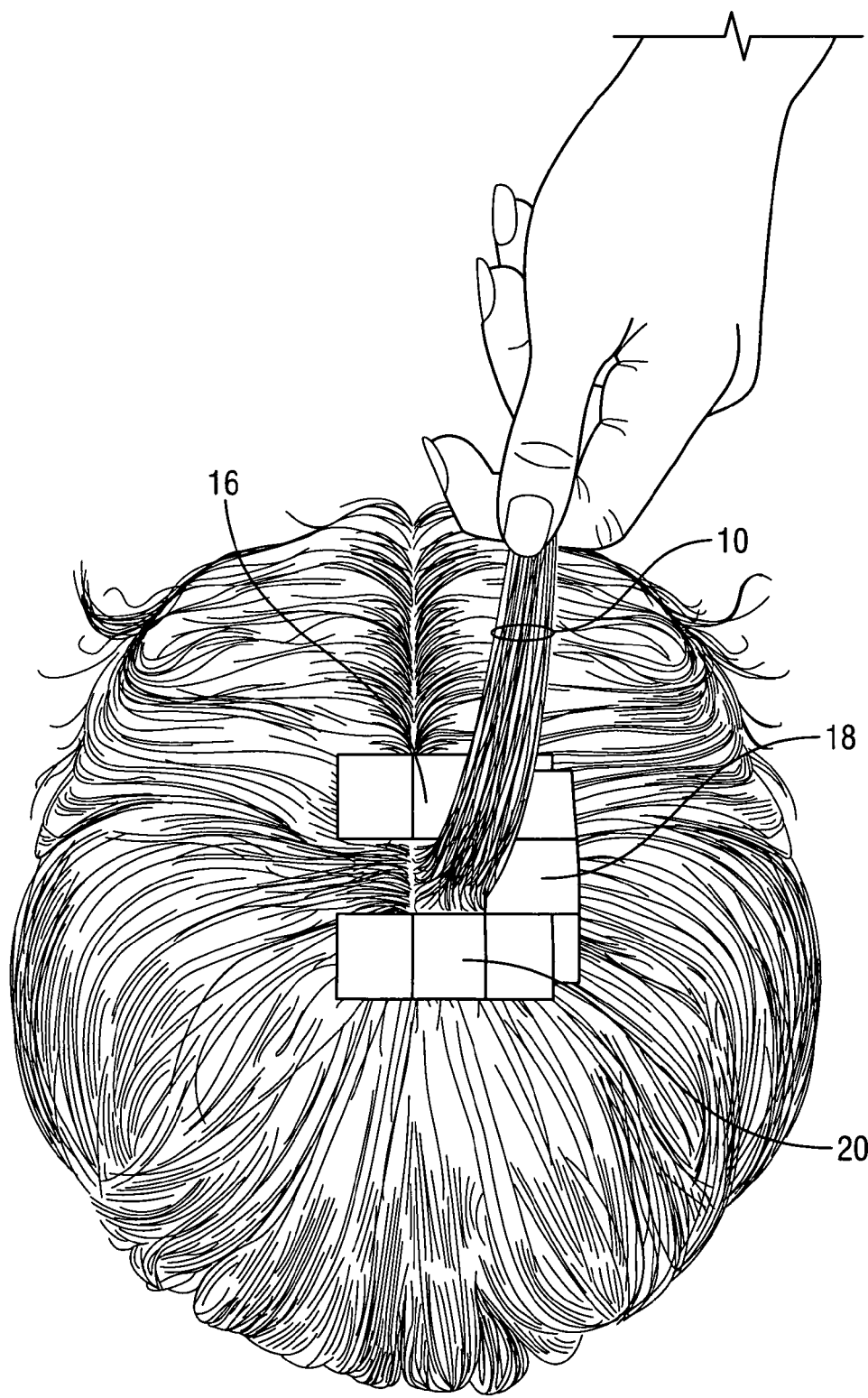
FIG. 3 is a top view of a scalp showing a section or bundle of hair that is combed from a delineated section of scalp and shows three sides of the section of scalp being delineated by gummed labels.
Figure 4:
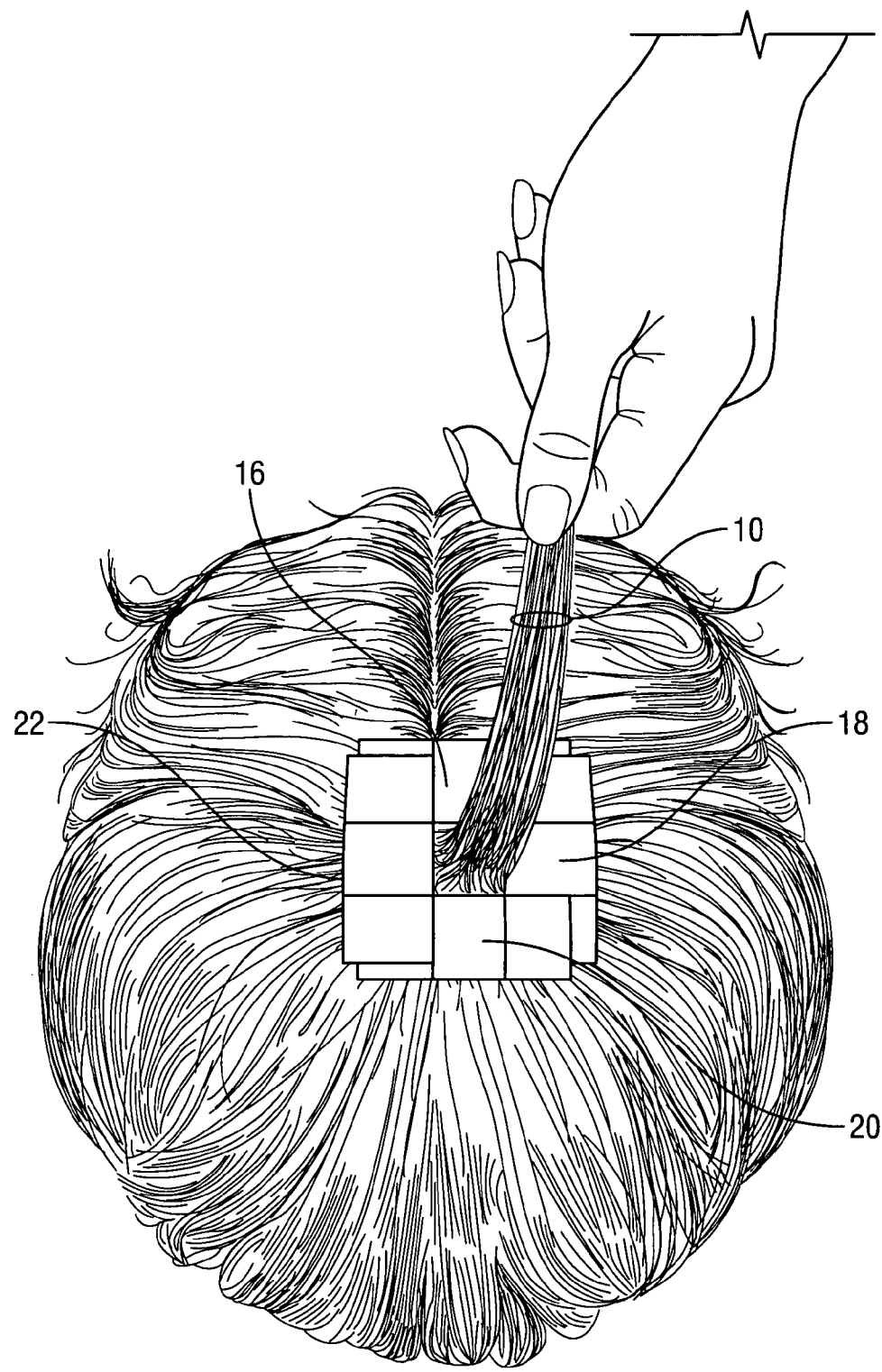
FIG. 4 is a top view of a scalp showing a section or bundle of hair that is combed from a delineated section of scalp and shows four sides of the section of scalp being delineated by gummed labels.

As shown in FIGS. 2–4, sequentially the delineated area of the scalp is fixed by gummed labels 18, 20 and 22. Each gummed label has a centimeter scale printed thereon so that the predetermined area, e.g., 2 square centimeters, can be measured and segregated by the gummed labels 16, 18, 20 and 22 from the rest of the hair on the scalp. The gummed labels 16, 18, 20 and 22 are printed with lines at intervals 2 cm apart scale. The color-coded lines are aligned with the edge of the preceding label and overlapped in a 4 step sequential fashion to create an isolated field of uncut hair that is 2 cm square.

Preferably, a 2×2 cm of scalp hair is manually isolated by combing the hair away from the designated square of hair-bearing scalp skin. This is done in a sequential fashion as described above. Care is taken to maintain a straight line at 90 degrees from the previous passage of the combing element 14.

Figure 5:
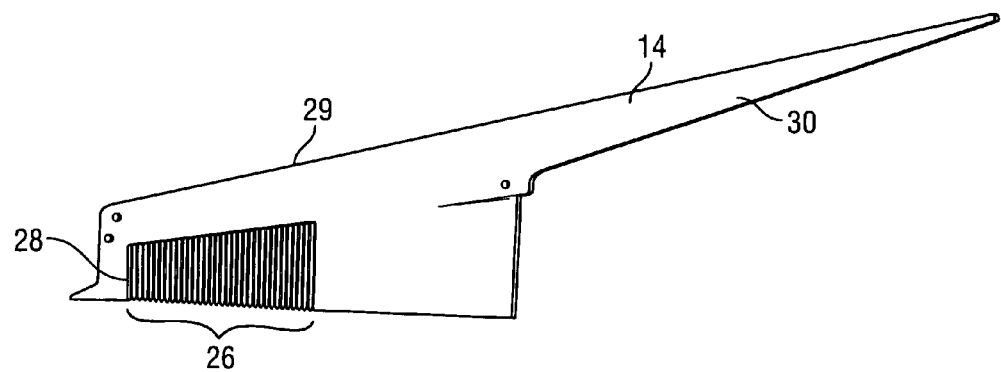
FIG. 5 is a plan view of one combing element.

The combing element 14 is shown in FIG. 5 and has a predetermined tine area 26, e.g., 2 cm. long, with tines 28 and an upwardly sloping top edge 29 extending to a handle 30.

Figure 6:
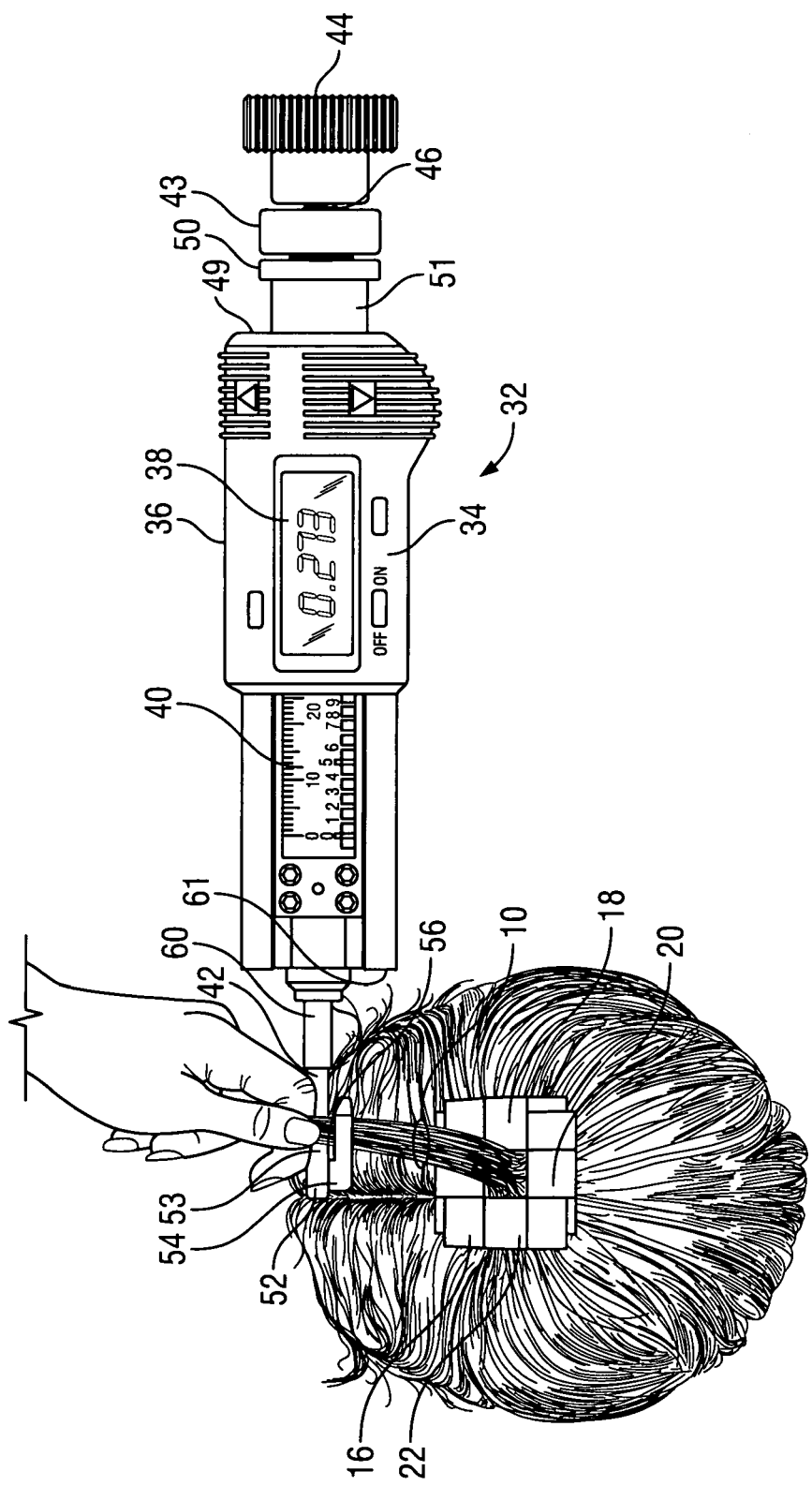
FIG. 6 is a top plan view of the scalp shown in FIG. 4 and a device constructed according to the teachings of the present invention for measuring the cross-sectional area of the bundle of hair.

A device 32 is provided, as shown in FIG. 6 for measuring the mass of hair in a bundle 10 from the 2 sq cm area of a hair bearing skin or scalp and compares that hair mass to the hair mass per sq. cm. in a permanent (normal) zone on the scalp.

The device 32 is an electronic caliper 34 having a body 36 with an electronic display 38 and a scale, gauge or analog display 40 for indicating the height or mass of hair in the hair bundle 10.

Figure 7:
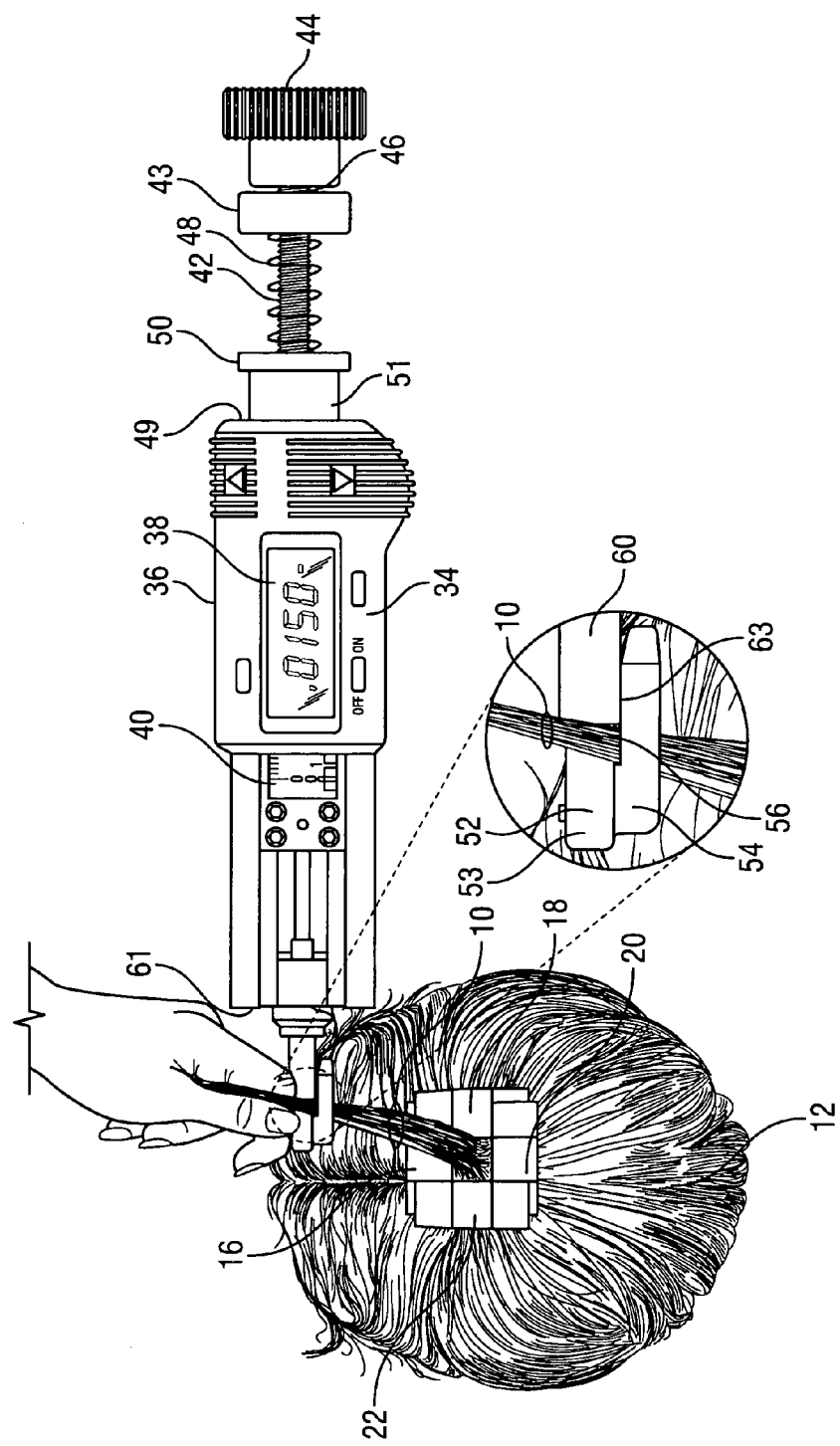
FIG. 7 is a top plan view of a scalp shown in FIG. 6 with a "J" shaped end of the device move toward a boss on the body of the device to measure the cross-sectional area of the bundle of hair positioned in a slot of the "J" shaped end.
Figure 8:
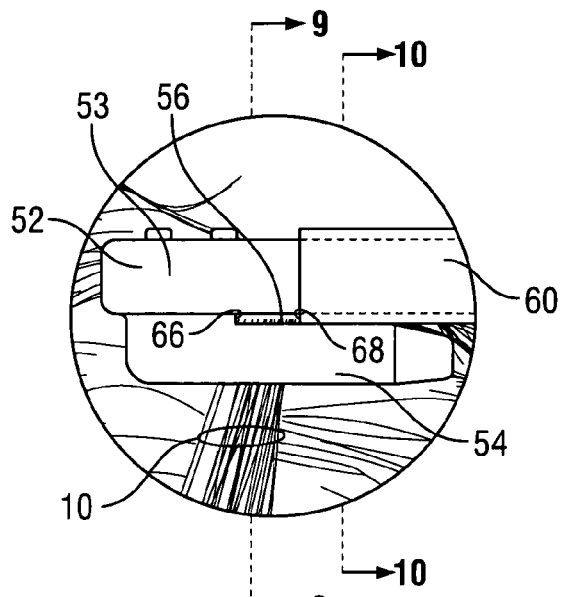
FIG. 8 is a fragmentary enlarged view of the hair trapped in the slot of the "J" shaped end.

The device 32 includes a piston or plunger 42 that extends through the body 36 and has a collar 43 thereon below a knob 44 at an outer end 46 of the plunger 42. A light weight return spring 48 (FIG. 7) bears against the collar 43 to urge the knob 44 away from an upper end 49 of the body 36 to push the plunger 42 upwardly. As shown a collar 50 between the spring 48 and the upper end 49 of the body of the body 36 is provided and has a reduced in diameter portion 51 that extends into the body 36.

It will be understood that the scale, gauge or analog display 40 moves with the plunger 42. Also, of course, the amount of movement of the plunger will be shown on the display 38.

The other end 52 of the plunger 42 has a "J" shape defined by a main leg 53 and a hook leg 54 with a slot 56 therebetween. The slot 56 can be 1 mm wide and 12 mm high.

Figure 9:
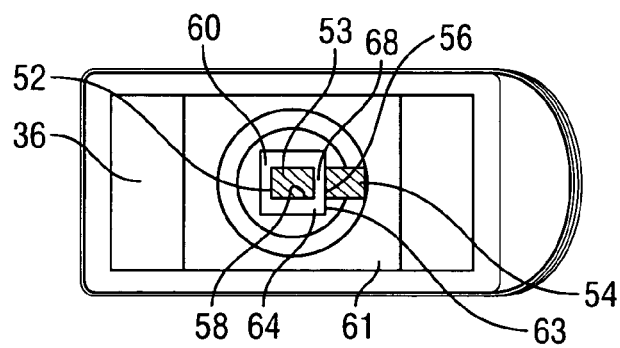
FIG. 9 is a cross-sectional view of the "J" shaped end taken along line 9–9 of FIG. 8.
Figure 10:
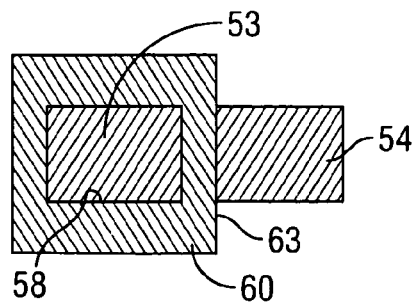
FIG. 10 is a cross-sectional view of a boss extending from the body of the device and in which the "J" shaped end is received.

The main leg 52 extends through a through bore 58 (FIG. 9) in a boss 60 at a lower end 61 of the body 36.

Figure 11:
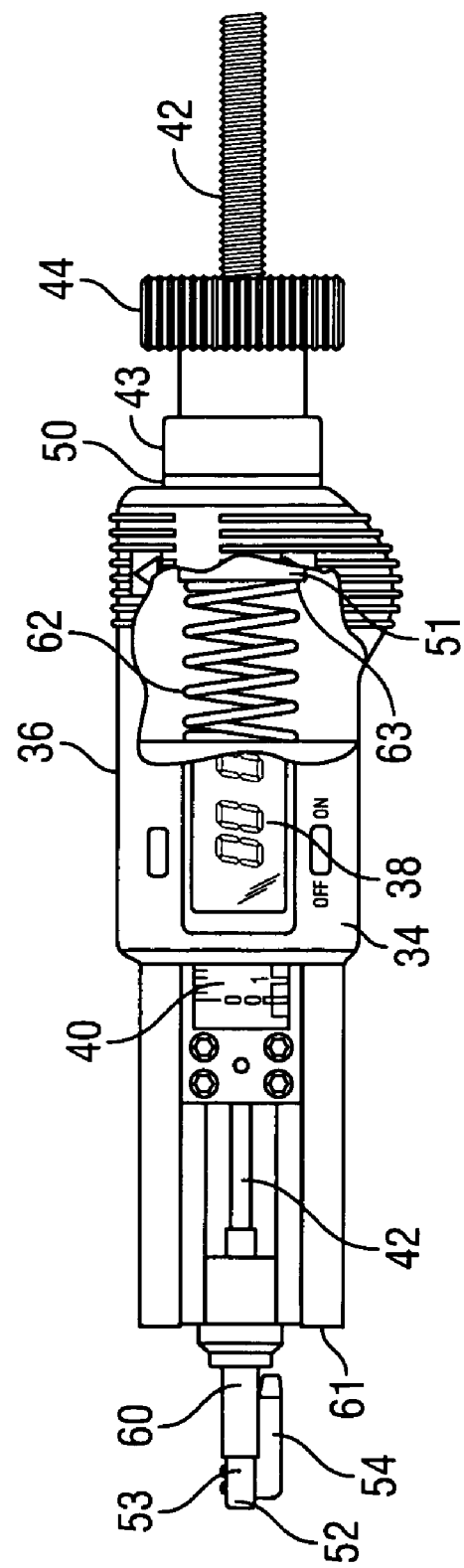
FIG. 11 is a plan view of the device without a bundle of hair in the slot of the "J" shaped end, shows the "J" shaped end moved over the boss, and is broken away to show a heavy compression spring In the body of the device.

As shown in FIG. 11 a heavy compression spring 62 in the body 36 bears against a lower end 63 of the reduced in diameter portion 51 of the collar 50.

A wall 64 of the boss 60 between the bore 58 and an outer surface 63 of the boss 60 is slidably received in the slot 56 upon relative movement between the boss 60 and the "J" shaped end 52.

The bundle of hair 10 is placed in the slot 56 and the knob 44 is screwed down on the plunger 42 and moves the reduced in diameter portion 51 of the collar 50 into the body 36 to compress the bundle of hair 10 between a bottom 66 of the slot 56 and an end surface 68 of the wall 54 (FIG. 9) with a predetermined compression established by the spring constant of the heavy spring 62 acting on the plunger 42. The end surface 68 defines an anvil 68 against which the bundle 10 of hair is compressed. In this way the device 32 defines a measuring device comprising the hair-holding slot 56, the "J" shaped end of the spring-loaded plunger 42 and the anvil 68.

The bundle or column 10 of hair is placed into the slot 66 and compressed against the anvil 68 in order to measure its height of the column or bundle 10 of hair. The anvil 68 and plunger are designed in a manner that always applies the same pressure to the column or bundle 10 of trapped hair. (This is accomplished with the heavy compression spring 62 bearing against the reduced in diameter portion of the collar 51) This is important because the hair bundle 10 is quite compressible. The mm height of the hair bundle or column 10 is read off a window on the electronic display 38 and/or off of the scale gauge or analog display 40. This arbitrary value shall be called the hair loss index or the density-diameter index. The procedure is performed in the balding area and the permanent area. The value for the balding area is divided by the value for the permanent area. The percent loss of hair mass in the balding is thus derived.

Oddly, in pattern balding (Androgenetic alopecia), the back and sides of the scalp are immune to the thinning process which doctors call miniaturization. So that on a balding scalp, the permanent horseshoe shaped fringe is populated with normal sized hairs (70 microns) with a normal density of 120–200 hairs per square cm. On the top of the scalp, in the areas of hair loss, the population of hairs ranges in size from 70 microns to 15 microns in diameter with a wide range of hairs per square cm.

The cumulative number of hairs per sq cm of scalp times their cumulative diameters equals a value that is best described as the hair mass. When the hair mass value of the balding zone is divided by the hair mass value of the normal permanent zone, the percent loss of hair mass in the balding area is derived. When the hair mass value in an area of loss is compared with a subsequent measurement of the same area at a time in the future, the percent hair loss or growth may be derived.

This information is very important to those who care for patients with hair loss, and those who develop drugs or devices that promote hair growth. Again it must be emphasized that although the length of the hair does contribute to the total visual mass of hair, it is not considered because it varies with the cut length of the hair (styling) which has no relevance to intended application of this patent.

From the foregoing description, it will be understood that the method and device of the present invention have a number of advantages, some of which have been described above and others of which are inherent in the method and device of the present invention.

Also modifications can be made to the method and device of the present invention without departing from the teachings of the present invention.

For example, a mark can be placed on the body 36 and another mark placed on the plunger 42 and a separate caliper can be used to measure the distance between the marks for determining the height of hair compressed in the slot 56.

The heavy spring 62 can be omitted and the knob 44 can be tightened with a torque wrench to place a predetermined amount of compression on the bundle 10 of hair.

A simple protrusion with an anvil at the end can used in place of the boss 60 and received in the slot 56.

A simpler device can be provided including a body with the slot 56 therein and a piston having the anvil 68 at one end can be provided and positioned to be received in the slot 56.

The body can be moved against the piston or the piston can be moved in and out of the slot 56.

The body and piston can be provided with a return spring, like spring 48, for holding the anvil 68 in the slot 56 until the spring is compressed to move the anvil 68 out of the slot 56.

If desired, side arms can be provided on the body, much like on a syringe, to facilitate gripping of the body while the piston or plunger is reciprocated or the knob 44 is rotated.

The non-isolated hair can be held down by other means, such as a ruler or hair clips instead of with gummed labels.

Further, the caliper can be mechanical or electrical electronic, can be attached to the body or plunger or can be separate from the device 32.

Accordingly, the scope of the invention is only to be limited as necessitated by the accompanying claims.

I claim:

1. A method of isolating a predetermined area of hair-bearing skin and measuring the combined cross section of uncut hair within the area comprising the steps of:
    preparing a pre-measured site using a combing element;
    isolating a bundle or column of hair from the site;
    peripherally positioning hair restraining elements adjacent the site to immobilize the non-isolated hair;
    providing a measuring device with a hair-receiving slot;
    placing the bundle or column of uncut hair in the slot;
    moving a bottom of the slot against an anvil of the device;
    measuring the height or mass of the compressed bundle or column of uncut hair in the slot; and,
    comparing the height or mass of hair measured with the height or mass of other hair measurements of a similar bundle or column of uncut hair.

2. The method of claim 1 wherein the similar bundle of hair is from the permanent hair area.

3. The method of claim 1 wherein the measurement of a similar bundle of hair was from a previously isolated bundle of hair from approximately the same of the site.

4. The method of claim 1 including the step of placing a predetermined compression on the anvil.

5. The method of claim 1 wherein the site is approximately 2 cm by 2 cm square.

6. The method of claim 1 wherein the slot is approximately 1 mm wide by 12 mm high.

7. The method of claim 1 wherein said hair restraining elements are calibrated gummed elements which are placed over the non-isolated hair.

8. A method for isolating an area of hair-bearing skin and measuring a combined cross section of hair in the area comprising the steps of:
    preparing a pre-measured site on the scalp;
    isolating a standardized bundle of uncut hair at the site;
    positioning hair restraining elements at the periphery of the site;
    compressing the bundle of hair with a measurable load while simultaneously measuring the height of the bundle of hair with a piston and cylinder device.

9. The method of claim 8 wherein said hair restraining elements are calibrated gummed elements which are placed over the non-isolated hair.

10. A device for measuring the cross-sectional area of uncut hair from a pre-measured area of hair-bearing skin, said device comprising a body, a plunger extending through said body and out one end of said body, a wall surface at said one end of said body, a compression spring associated with said body for applying a predetermined amount of pressure on said plunger, said plunger extending through said wall surface and having a "J" shaped end defined by a main leg portion extending through said wall surface and a hook leg portion, said two leg portions defining a hair receiving slot therebetween, said wall surface defining an anvil which is received in said slot and against which hair received in said slot is compressed, and measuring means associated with said body and associated with said plunger for measuring the extent of movement of said plunger.

11. The device of claim 10 wherein said slot is approximately 1 mm wide and 12 mm high.

12. The device of claim 10 wherein said measuring means include one of an integrated or separate electronic caliper with a visual display for indicating the height of compressed hair in said slot when said "J" shaped end of said plunger is moved toward said anvil with a bundle of hair in said slot.

13. The device of claim 10 wherein said measuring means include a scale, gauge or analog display for indicating the height of compressed hair in said slot when said "J" shaped end of said plunger is moved toward said anvil with a bundle of hair in said slot.

14. The device of claim 10 including a knob at the other end of said plunger which can be gripped and pushed by a hand for moving said "J" shaped end against a spring force away from said anvil to open said slot for receiving a bundle of hair and released for moving said "J" shaped end with the spring force toward said anvil for compressing the bundle of hair between a bottom of said slot and said anvil.

15. The device of claim 14 wherein said "J" shaped end is spring loaded so that after the "J" shaped end is pushed out of said body, said "J" shaped end will return to it's at rest position and the compression spring is used to compress the bundle of hair.

16. A device for measuring the cross-sectional area of uncut hair from a pre-measured area of hair-bearing skin, said device comprising a body having a generally rectangular slot for receiving a bundle of hair, an anvil positioned adjacent said slot for being received in said slot upon relative movement between said anvil and said body, a compression spring associated with one of said body or said anvil and mechanically limited to place no more than a predetermined, precise amount of compressive force on variable-sized bundles of hair placed in said generally rectangular slot and a mechanical mechanism for causing relative movement between said body having said slot and said anvil to compress the bundle of hair with no more than the predetermined, precise amount of compressive force and without hand compression.

17. The device of claim 16 including a measuring device associated with said device for measuring the amount of movement between said body and said anvil when a bundle of hair is received in said slot and compressed in said slot.

18. The device of claim 16 including a return spring for normally holding said anvil in said slot, and said return spring being compressible to permit said anvil to be moved out of said slot to permit a bundle of hair to be received in said slot.

19. The device of claim 16 wherein said body is partially U-shaped with said slot being in the U.

20. The device of claim 16 wherein said body is at least partially J-shaped with said slot being in the J.

21. A method of isolating a predetermined area of hair-bearing skin and measuring the combined cross section of uncut hair within the area comprising the steps of:
    preparing a pre-measured site using a combing element;
    isolating a bundle or column of uncut hair from the site;
    providing a slot having a width of 1 mm;
    placing the bundle or column of uncut hair in the slot;

providing mechanical structure for moving a bottom of the slot against an anvil of the device with a precise predetermined compressive force;

measuring the height or mass of the compressed bundle or column of uncut hair in millimeters in the slot; and, comparing the height or mass of hair measured with the height or mass of other hair measurements of a similar bundle or column of hair.

22. A device for measuring the cross-sectional area of uncut hair from a pre-measured area of hair-bearing skin, said device comprising a body having a slot which is 1 mm wide for receiving a bundle of uncut hair, an anvil positioned adjacent said slot for being received in said slot upon relative movement between said anvil and said body, a compression spring associated with one of said body or said anvil and mechanically limited to place no more than a predetermined, precise amount of compressive force on variable-sized bundles of hair placed in said slot and a mechanical mechanism for causing relative movement between said body having said slot and said anvil to compress the bundle of hair with no more than the predetermined, precise amount of compressive force.

23. A method of isolating a predetermined area of hair-bearing skin and measuring the combined cross section of uncut hair within the area comprising the steps of:

preparing a pre-measured site using a combing element;

isolating a bundle or column of hair from the site;

peripherally positioning hair restraining elements adjacent the site to immobilize the non-isolated hair;

providing a measuring device with a hair-receiving slot;

placing the bundle or column of uncut hair in the slot;

providing mechanical structure for moving a bottom of the slot against an anvil of the device with a precise predetermined compressive force;

measuring the height or mass of the compressed bundle or column of uncut hair in the slot; and, comparing the height or mass of hair measured with the height or mass of other hair measurements of a similar bundle or column of uncut hair.

24. A method for isolating an area of hair-bearing skin and measuring a combined cross section of hair in the area comprising the steps of:

preparing a pre-measured site on the scalp;

isolating a standardized bundle of uncut hair at the site;

positioning hair restraining elements at the periphery of the site;

providing mechanical structure for compressing the bundle of hair with a precise measurable load while simultaneously measuring the height of the bundle of hair with a piston and cylinder device.

* * * * *